United States Patent
Knuebel et al.

(10) Patent No.: US 11,980,279 B2
(45) Date of Patent: May 14, 2024

(54) SYSTEM AND METHOD FOR ESTABLISHING A USER-SPECIFIC HAIR TREATMENT

(71) Applicant: Henkel AG & Co. KGaA, Duesseldorf (DE)

(72) Inventors: Georg Knuebel, Duesseldorf (DE); Antje Gebert-Schwarzwaelder, Neuss (DE); Thomas Foerster, Duesseldorf (DE)

(73) Assignee: HENKEL AG & CO. KGAA, Duesseldorf (DE)

(*) Notice: Subject to any disclaimer, the term of this patent is extended or adjusted under 35 U.S.C. 154(b) by 1443 days.

(21) Appl. No.: 16/311,592

(22) PCT Filed: Jul. 4, 2017

(86) PCT No.: PCT/EP2017/066579
§ 371 (c)(1),
(2) Date: Dec. 19, 2018

(87) PCT Pub. No.: WO2018/007357
PCT Pub. Date: Jan. 11, 2018

(65) Prior Publication Data
US 2019/0183232 A1  Jun. 20, 2019

(30) Foreign Application Priority Data

Jul. 5, 2016 (DE) .................. 10 2016 212 202.9
Dec. 1, 2016 (DE) .................. 10 2016 223 916.3

(51) Int. Cl.
| G09B 19/00 | (2006.01) |
| A45D 44/00 | (2006.01) |
| A61B 5/00 | (2006.01) |
| A61B 5/103 | (2006.01) |
| A61Q 5/00 | (2006.01) |
| G06Q 20/20 | (2012.01) |

(52) U.S. Cl.
CPC ............ *A45D 44/00* (2013.01); *A61B 5/0075* (2013.01); *A61B 5/1032* (2013.01); *A61B 5/448* (2013.01); *A61B 5/7246* (2013.01); *A61Q 5/00* (2013.01); *G06Q 20/20* (2013.01); *A45D 2044/007* (2013.01); *A61B 2503/12* (2013.01); *A61B 2560/0223* (2013.01)

(58) Field of Classification Search
CPC ........ A61B 5/448; G09B 19/20; G09B 19/00; G09B 19/0023; G09B 19/10
USPC .......................................................... 434/94
See application file for complete search history.

(56) References Cited

U.S. PATENT DOCUMENTS

| 6,058,943 | A | 5/2000 | Davis-Harris | |
| 2002/0010556 | A1* | 1/2002 | Marapane | G01J 3/526 |
| | | | | 702/32 |
| 2003/0106564 | A1* | 6/2003 | Olshavsky | A61Q 5/08 |
| | | | | 132/207 |
| 2006/0281994 | A1* | 12/2006 | Miyamae | G01N 21/3563 |
| | | | | 600/473 |
| 2014/0118521 | A1 | 5/2014 | Conti | |
| 2016/0175620 | A1* | 6/2016 | Landa | A61K 8/40 |
| | | | | 8/408 |
| 2017/0119130 | A1* | 5/2017 | Witchell | G01N 21/31 |

FOREIGN PATENT DOCUMENTS

| CN | 1440503 | A | | 9/2003 | |
| CN | 103635176 | A | | 3/2014 | |
| CN | 103649750 | A | | 3/2014 | |
| DE | 102016212202 | A1 | | 1/2018 | |
| DE | 102016222193 | A1 | | 5/2018 | |
| JP | 2003270138 | A | * | 9/2003 | ............ G01N 21/35 |
| JP | 2003270138 | A | | 9/2003 | |
| JP | 2003344279 | A | | 12/2003 | |
| JP | 2010112788 | A | | 5/2010 | |
| WO | 2010076104 | A2 | | 7/2010 | |
| WO | 2015166403 | A1 | | 11/2015 | |

OTHER PUBLICATIONS

Miyamae et al.: "A Non-Destructive Method for Assessing Interior and Surface Hair Damage by Near Infrared Spectroscopy", Jan. 2007, POLA Chemical Industries, Inc., Department of Chemistry, School of Science and Technology, Kwansei-Gakuin University, Japan.
Miyamae et al.: "Evaluation of Physical Properties of Human Hair by Diffuse Reflectance Near-Infrared Spectroscopy", Applied Spectroscopy, vol. 61, 2007, No. 2, pp. 212-217, Japan.
Rashaid et al.: "Amino acid composition of human scalp hair as a biometric classifier and investigative lead", Analytical Methods, vol. 7, 2015, pp. 1707-1718.
Takada et al.: "Influence of Oxidative and/or Reductive Treatment on Human Hair (I): Analysis of Hair-Damage after Oxidative and/or Reductive Treatment", Journal of Oleo Science, vol. 52, 2003, No. 10, pp. 541-548, Japan.
EPO, International Search Report issued in International Application No. PCT/EP2017/066579, dated Oct. 5, 2017.

* cited by examiner

*Primary Examiner* — Kurt Fernstrom
(74) *Attorney, Agent, or Firm* — Lorenz & Kopf, LLP

(57) ABSTRACT

The present disclosure relates to a method for determining a user-specific hair treatment with determination and inclusion of the state of the hair. To this end, the content of at least one hair constituent is firstly determined with the aid of near-infrared and/or infrared and/or VIS and/or Raman spectra of the hair of an individual and a hair state is derived via a calibration model. Individual treatment advice is output on the basis of the determined hair state.

20 Claims, No Drawings

SYSTEM AND METHOD FOR ESTABLISHING A USER-SPECIFIC HAIR TREATMENT

CROSS-REFERENCE TO RELATED APPLICATION

This application is a U.S. National-Stage entry under 35 U.S.C. § 371 based on International Application No. PCT/EP2017/066579, filed July 4, 2017 which was published under PCT Article 21(2), which claims priority to German Application No. 10 2016 223 916.3, filed Dec. 1, 2016, which claims priority to German Application No. 10 2016 212 202.9, filed Jul. 5, 2016, which are all hereby incorporated in their entirety by reference.

TECHNICAL FIELD

The present disclosure relates to a method for determining a user-specific hair treatment.

BACKGROUND

Human hair includes proteins, lipids, water, trace elements and pigments. The fibre protein keratin is the primary constituent of hair. The lipids that are present in human hair are either free or covalently bonded. Melanins are reddish, brown or black pigments that give the hair color.

The quantitative determination of the amino acids, covalently bonded lipids and the melanins requires the solubilization or total hydrolysis of the keratin. This can be achieved for example by employing acid or alkali total hydrolysis or by employing enzymatic degradation. The content of the individual amino acids, lipids or melanins can be determined by employing chromatographic methods, such as high-performance liquid chromatography (HPLC), gas chromatography (GC), thin-layer chromatography (TLC), or ion exchange chromatography (IEC).

The water content in hair can be determined for example by employing Karl-Fischer titration.

Ambient influences (in particular UV light radiation), cosmetic treatments (for example bleaching, permanent waving or heat treatments) or certain diets (in particular low-protein diets) mean that the composition in respect of one or more constituent(s) of hair changes unfavorably.

This can cause the hair to lack shine and hold or can cause it to feel dry and brittle and thus be difficult to manage.

There are many haircare products on the market that are intended to improve different hair properties or parameters, such as shine. In many cases, however, the user of such products does not know what state their own hair is in. For example, the user often does not know how strong their hair is or in what way is damaged. This can mean that the user resorts to products that are less suitable for their specific case and is dissatisfied with the efficacy of these products after using them.

A determination of the composition of the hair in respect of the contained amino acids, lipids and melanins and also the water content may therefore be of great importance.

As described above, a large number of physical and chemical-analytical methods are available to a researcher in the academic and industrial field for determining the composition of hair.

However, all of these methods are complicated and require a costly equipment set-up, such that they are not available to an end consumer.

Users of products increasingly desire a product adapted to their individual requirements. This is also true in particular for beauty products such as skin and/or hair treatment agents.

BRIEF SUMMARY

A method for the individualized treatment of hair is provided herein. The method includes the step of determining a content of hair constituent of a number of samples of hair with a different hair state by a chromatographic or colorimetric process. The method further includes the step of recording near-infrared and/or infrared and/or VIS and/or Raman spectra of the samples of hair with a different hair state. The method further includes creating a calibration model which produces a correlation between near-infrared and/or infrared and/or VIS and/or Raman spectra and the content of hair constituent. The method further includes recording a near-infrared and/or an infrared and/or a VIS and/or a Raman spectrum of hair of an individual. The method further includes determining the state of the hair of the individual on the basis of the calibration model. The method further includes outputting individual treatment advice regarding the hair of the individual depending on the determined hair state. The hair constituent is selected from the group of amino acids, lipids, melanins, water and mixtures thereof.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was therefore to provide a method for determining individual hair treatment advice that allows an end user to determine the content of at least one constituent of their hair in a simple manner and to obtain hair treatment advice adapted thereto.

This object is achieved by a method for determining an individualized hair treatment comprising the following steps:

a) determining the content of hair constituent of a number of samples of hair with a different hair state by employing a chromatographic or colorimetric process;

b) recording near-infrared and/or infrared and/or VIS and/or Raman spectra of the samples of hair with a different hair state;

c) creating a calibration model which produces a correlation between near-infrared and/or infrared and/or VIS and/or Raman spectra and the content of hair constituent;

d) recording a near-infrared and/or an infrared and/or a VIS and/or a Raman spectrum of hair of an individual;

e) determining the state of the hair of the individual on the basis of the calibration model; and f) outputting individual treatment advice regarding the hair of the individual depending on the determined hair state, wherein the hair constituent is selected from the group of amino acids, lipids, melanins, water and mixtures thereof.

The term hair within the scope of this application comprises keratin-containing fibres, such as furs, wool and feathers, but in particular human hair.

The near-infrared and/or infrared and/or VIS and/or Raman spectroscopy allows the direct, destruction-free determination of the content of a hair constituent without complex sample preparation and without changing or destroying the hair by analysis of the structure thereof. This has the advantage that the result can be very quickly obtained and the hair can be subjected to a treatment once the content of hair constituent has been determined. A further advantage is that the near-infrared and/or infrared and/or VIS and/or Raman spectroscopy can be performed on hair located on the head of the individual.

Human hairs, in addition to the 20 canonical amino acids glycine, alanine, valine, isoleucine, leucine, phenylalanine, tyrosine, lysine, arginine, histidine, aspartic acid, glutaminic acid, threonine, serine, glutamine, asparagine, methionine, cysteine, proline and tryptophan, also contain the amino acids cystine, ornithine and citrulline. It is preferred, accordingly, that the hair constituent of which the content is determined is an amino acid selected from the group consisting of glycine, alanine, valine, isoleucine, leucine, phenylalanine, tyrosine, lysine, arginine, histidine, aspartic acid, glutaminic acid, threonine, serine, glutamine, asparagine, methionine, cysteine, proline and tryptophan, cystine, ornithine, citrulline and mixtures thereof.

It is particularly preferred that the hair constituent of which the content is determined is an amino acid selected from the group consisting of cysteine, methionine, glutamine, arginine, tyrosine, cystine and mixtures. The content of these amino acids, in particular on the L-form of these amino acids, has a great influence on the state of hair.

Lipids that are contained in human hair comprise hydrocarbons, squalene, wax esters, triglycerides, fatty acids, cholesterol, cholesterol sulfate, ceramides and 18-methyl eicosanoic acid. It is preferred, accordingly, that the hair constituent of which the content is determined is a lipid selected from the group consisting of hydrocarbons, squalene, wax esters, triglycerides, fatty acids, cholesterol, cholesterol sulfate, ceramides and 18-methyl eicosanoic acid (18-MEA) and mixtures thereof.

It is particularly preferred that the hair constituent of which the content is determined comprises a lipid which is 18-methyl eicosanoic acid.

Melanin occurs in humans in particular in two variants: a brown-blackish variant (eumelanin) which derives from the amino acids tyrosine and levodopa, and a lighter yellowish-reddish variant (pheomelanin) which contains sulfur. It is preferred, accordingly, that the hair constituent of which the content is determined is a melanin selected from the group consisting of eumelanin, pheomelanin and mixtures thereof.

In a very particularly preferred embodiment as contemplated herein the content of two or more hair constituents is determined. The two or more hair constituents are selected from the group consisting of amino acids, lipids, melanins, water and mixtures thereof. The two or more hair constituents can be selected here from one compound class or a plurality of compound classes. This means that the content of two or more amino acids, of two or more lipids, or of eumelanin and pheomelanin can be determined. Alternatively, the two or more hair constituents can be selected from different compound classes. For example, the contents of one or more amino acid(s) and one or more lipid(s) can thus be determined. Alternatively, the contents of one or more amino acid(s) and one or more melanin(s) can be determined. In a further alternative the contents of one or more lipid(s) and one or more melanin(s) can be determined. In yet a further alternative the contents of one or more amino acid(s), one or more lipid(s) and one or more melanin(s) are determined.

In yet a further alternative one hair constituent is water and, in addition to the water content, the content(s) of one or more amino acid(s), one or more lipid(s) and/or one or two melanin(s) is/are determined.

The claimed method firstly requires the creation of a calibration model. To this end, in a step a), the content of a hair constituent of a number of samples in different states is firstly determined by employing an independent, for example chromatographic process, for example HPLC, or a colorimetric process. The content of water in hair samples can be determined for example by employing the microwave measurement method.

In a step b) near-infrared and/or infrared and/or VIS and/or Raman spectra of the samples of hair are then recorded.

In step c) a calibration model is created which produces a correlation between the near-infrared and/or infrared and/or VIS and/or Raman spectra of the samples (calibration spectra) and the content of constituent of the samples that was determined by employing an independent chromatographic, colorimetric or electromagnetic process. The creation of the calibration model can also comprise the recording, for the plurality of calibration hair samples, of a calibration spectrum of at least part of the near-infrared and/or infrared and/or VIS and/or monochromatic light that is reflected and/or scattered by the calibration hair sample during exposure of the calibration hair sample to near-infrared and/or infrared and/or VIS and/or monochromatic light, determining of the hair state of the calibration hair sample by employing an independent chromatographic, colorimetric or electromagnetic process, allocating of a hair state to the calibration spectrum, and determining of a correlation between the plurality of calibration spectra and the plurality of states.

Steps a) and b) do not necessarily have to be carried out successively or in that order. Thus, step b) can be carried out first, followed then by step a).

In a preferred embodiment the calibration model from steps a) to c) is present in the form of stored information on a local data carrier or in a cloud. A local data carrier in the sense of this application comprises all physical carrier substances on which data can be recorded. In a particularly preferred embodiment the data carrier is identical to the data processing device to which the (N)IR, VIS, (N)IR/VIS or Raman spectrometer for recording near-infrared and/or infrared and/or VIS and/or Raman spectra of the hair is connected. This can be in particular a smart phone, a tablet, a laptop, a smart mirror or a computer. In an alternative embodiment the calibration model from steps a) to c) is present in the form of stored information in a cloud.

By use of mathematical models, a mathematical model can be created by measurement of calibration hair samples which have a content of hair constituent determined on the basis of a known analytical method which then allows a calculation of a content of hair constituent and thus a conclusion of the state of the hair in a hair sample, also referred to as a braid, from the individual on the basis of the recorded NIR, IR and/or VIS and/or Raman spectrum. An analysis of the spectrum and use of the model can be performed here for example (with suitable apps) by employing known data processing devices, such as smart phones, tablets, or the like.

The mathematical model may be an artificial system that for example learns from the calibration hair samples and can generalise these once the learning phase is complete. This means that the examples are not simply memorised, but patterns and laws are identified in the learning data. Different approaches can be followed to this end. For example, a monitored learning, a partially monitored learning, an unmonitored learning, a corroborated learning and/or active learning can be used, in particular in conjunction with deep learning methods. Monitored learning can be implemented for example by employing an artificial neural network (for example a recurrent neural network) or by employing a support vector machine. Unmonitored learning can also be implemented for example by employing an artificial neural network (for example an auto encoder).

Further factors, in particular categorical factors, such as ethnicity of the individual, age of the individual (as category or metrically), hair color of the individual (as category or metrically) can also be taken into consideration in order to optimise the calibration model.

In the further course of the method, in step d) a near-infrared and/or infrared and/or VIS and/or Raman spectrum of the hair of an individual is recorded. This can be achieved for example in such a way that, during the exposure of a hair sample of the hair of the individual to near-infrared and/or infrared and/or VIS light and/or monochromatic light, a spectrum of at least part of the near-infrared and/or infrared and/or VIS light and/or monochromatic light that is reflected and/or scattered by the hair sample is recorded. A plurality of near-infrared and/or infrared and/or VIS and/or Raman spectra per measurement point are thus preferably recorded in step d) and averaged in each case.

In step e) the content of the hair constituent of the hair of the individual is determined on the basis of the calibration model created in steps a) to c). The hair state can be derived from the determined content of hair constituent. The derived hair state can include, for example, brittle, lacklustre, oxidatively damaged, heat-damaged, chemically damaged, dry, moist, greasy, hydrophilic, high in melanin, low in melanin or normal. The chemical damage may additionally be distinguished according to the type of damage, such as damage by permanent wavers, straighteners and/or relaxers.

To this end, at least part of the near-infrared and/or infrared, VIS and/or Raman spectrum of the hair of the individual is compared with the calibration model for example, and the content of hair constituent of the hair and/or hair state are/is determined/allocated.

In a further advantageous embodiment the near-infrared and/or infrared and/or VIS and/or Raman spectra of the hair of an individual are/is recorded at different positions along the hair. The near-infrared and/or infrared and/or VIS and/or Raman spectra can thus be recorded at the start of and/or in the middle and/or at the tips of the hair. Accordingly, the individual hair state can be determined for each of these positions.

Near-infrared spectroscopy, similarly to other vibrational spectroscopies, is based on the excitation of molecule vibrations by electromagnetic radiation in the (near) infrared range. In near-infrared spectroscopy the detection takes place in the near infrared (780-2,500 nm or approximately 12,800-4,000 $cm^{-1}$) Hereinafter, the term near-infrared (NIR) shall be used for light with a wave number in a range of from about 12,800 to about 4,000 $cm^{-1}$ and the term infrared (IR) shall be used for light with a wave number in a range of from about 3,999 to about 400 $cm^{-1}$.

Near-infrared (NIR) spectra and/or an infrared (IR) spectrum can be obtained for example by employing ATR (attenuated total reflection) (near-)infrared spectroscopy.

VIS spectroscopy uses light with a wavelength in the range of from about 380 to about 780 nm, which is also referred to as "visible light" (VIS).

Raman spectroscopy examines the inelastic scattering of light at molecules or fixed bodies (Raman scattering). Raman scattering is created by the interaction of electromagnetic radiation and the electron shell of the molecules and in contrast to (N)IR and VIS spectroscopy is practically independent of the wavelength of the excitation radiation. In Raman spectroscopy the material to be examined is irradiated with monochromatic light, usually from a laser.

In a preferred embodiment of the method two or more spectroscopy types are used. The recording of the spectra by employing different spectroscopy types can be performed simultaneously, that is to say in one measurement step, for example by spectrometers that can perform two or more spectroscopy types, or in two or more measurement steps. For example, the NIR, IR and VIS spectra of hair can thus be recorded simultaneously, for example using an (N)IR/VIS spectrometer. Alternatively, an NIR spectrometer can be used first, followed then by a Raman spectrometer, for example By use of miniaturised (N)IR spectrometers, (N)IR sensors, VIS spectrometers, VIS sensors, Raman spectrometers, Raman sensors, (N)IR/VIS spectrometers and/or (N)IR/VIS sensors and the connection thereof to a mobile data processing device, the method and in particular step d) of the method can be performed for example in the private field by the individual themself, by any person at a point of sale (POS) of hair treatment agents, or by a hairdresser. In a preferred embodiment the mobile data processing device is a smart terminal, for example a smart phone, a tablet or a laptop.

The (N)IR spectrometers, VIS spectrometers and/or (N)IR/VIS spectrometers and/or Raman spectrometers can also be provided in particular in mobile form, for example in the form of hand-held spectrometers or attachment spectrometers.

An example of a suitable hand-held spectrometer is the "MicroNIR OnSite" from the company Viavi Solutions Inc. This spectrometer is supplied with power and controlled by a tablet or a laptop via a USB connection. This hand-held spectrometer makes it possible to record the near-infrared and/or infrared spectra of the hair of an individual in real time with a measurement time of between about 0.25 and about 0.5 seconds. The spectrometer comprises two integrated vacuum tungsten lamps and an InGaAs photodiode array with 128 pixels. The "MicroNIR OnSite" operates in a wave number range of from about 6,060 to about 10,526 $cm^{-1}$. The distance between the hair and the glass of the hand-held spectrometer can be between 0 and about 15 mm, wherein a distance of about 3 mm is preferred.

In one embodiment as contemplated herein the entire method for determining an individualized hair treatment is performed by the tablet or the laptop which supplies power to and controls the "MicroNIR OnSite" spectrometer. Alternatively, the obtained spectroscopic data can be sent to a further (mobile) data processing device, in particular a further smart terminal, which them performs the method for determining an individualized hair treatment. The spectroscopic data can be transmitted for example wirelessly by employing WLAN (WiFi) or Bluetooth.

A further suitable hand-held spectrometer is the "i-Spec Nano" by the company B&W Tek. The spectrometer is supplied with power via a USB connection and a (mobile) data processing device connected thereto or via a battery. The spectrometer comprises a light source and operates in a wave number range of from about 4,545 to about 7,692 $cm^{-1}$. The spectroscopic data is transmitted to a (mobile) data processing device, which then performs the method for determining an individualized hair treatment, wirelessly by employing WLAN (WiFi) or Bluetooth.

The "QualitySpec Trek" NIR/VIS hand-held spectrometer from the company ASD Inc. is also suitable. It operates in a wave number range of from about 28,571 to about 400 cm$^{-1}$ (350 0 2,500 nm).

A further suitable hand-held spectrometer is the "SCiO by Consumer Physics", which displays the spectroscopic data on a smart terminal with the aid of the integrated app "SpectroScan". The hand-held spectrometer operates in the short-wave range of NIR, more specifically at wave numbers of from about 9,090 to about 14,285 cm$^{-1}$ (corresponds to about 700 to about 1,100 nm). The measured data is evaluated with the aid of a cloud, in which a material database, chemometric models and algorithms are stored, for example.

Further hand-held spectrometers are also obtainable from the company Attonics Systems which operate either in the wave number range from about 9,090 to about 26,315 cm$^{-1}$ (VIS-NIR) or from about 3,333 to about 10,000 cm$^{-1}$ (NIR). These spectrometers are based on interferometers and have a high light throughput and a high spectral resolution (<5 nm for VIS-NIR spectrometer and <20 nm for the NIR spectrometer). The spectrometers have a multi-phase shift array (MPA) chip and an optical arrangement in a circular tube. The spectrometers are also compatible with mobile data processing devices.

A further suitable, miniaturised NIR spectrometer can be found integrated in the smart phone H2 from the company Changhong.

Further examples of VIS-NIR spectrometers are the miniature spectrometers "USB2000-VIS-NIR" and "USB4000-VIS-NIR" from the company Ocean Optics. These spectrometers operate with a wavelength range of from about 350 to about 1,000 nm. The spectrometers are connected via a USB connection to a data processing device.

In addition, there are a series of NIR sensors or NIR evaluation modules that can be used in hand-held spectrometers. Suitable NIR evaluation modules are the "DLP® NIRscan" and "DLP® NIRscan Nano" modules from the company Texas Instruments. These have two tungsten lamps and InGaAs photodiodes as detectors. The module "DLP® NIRscan" operates in a wave number range of from about 4,016 to about 7,407 cm$^{-1}$ and the module "DLP® NIRscan Nano" in the range of from about 5,882 to about 11,111 cm$^{-1}$. The spectroscopic data is communicated wirelessly via Bluetooth Low Energy. With the aid of "Software Developer Kits" (SDK), for example the Open Source SDK from KST Technologies, apps can be developed which evaluate or further process the spectroscopic data.

Further suitable NIR sensors are obtainable under the name "NeoSpectra" from Si-Ware Systems. Specific sensors include: NeoSpectra SW62221-1.7, NeoSpectra SW62221-2.1 and NeoSpectra SW62221-2.5, which operate in different wave number ranges.

A suitable hand-held Raman spectrometer is the "Bravo" Raman spectrometer from the company Bruker. The Raman spectrometer operates in a spectral range of from about 300 to about 3,200 cm$^{-1}$ and comprises technology for suppressing fluorescence signals. The excitation is performed by employing two temperature-controlled diode lasers. The spectroscopic data can be transmitted to a (mobile) data processing device, which then performs the method for determining an individualized hair treatment, wirelessly by employing WLAN (WiFi) or via a network cable.

It is preferred in particular if a hand-held (N)IR/VIS spectrometer which transmits the spectroscopic data wirelessly by employing WLAN (WiFi) or Bluetooth is used in the method for determining an individualized hair treatment.

It can be preferred if the at least part of the near-infrared light and/or infrared light and/or VIS light and/or monochromatic light has a (near-infrared) wave number range of from about 12,500 cm$^{-1}$ to about 4,000 cm$^{-1}$ (corresponds to about 800 to about 2,500 nm). The absorptions of liquid water are within this range (about 836 nm, about 970 nm, about 1200 nm, about 1,470 nm and about 1,900 nm). Further (vibrational) absorptions of liquid water are located at about 401 nm, about 449 nm, about 514 nm, about 606 nm, about 660 nm, about 739 nm, about 2.87 µm, about 3.05 µm, about 4.65 µm, about 6.08 µm, about 15 µm and about 25 µm.

In a preferred embodiment step d) is controlled by a smart terminal. Here, it is preferred if the method is controlled by an app installed beforehand on the smart terminal. Smart terminals comprise smart phones or tablets, in particular.

Within the scope of this application a computer program that is used to process or to assist a non-system-related functionality is referred to as an "app". The term "app" in particular comprises application software for smart terminals such as smart phones and tables ("mobile app") and also desktop application software. The app can be a native app which functions merely on a platform, or a platform-independent web, hybrid or cross platform.

The app may particularly preferably be downloaded via a QR code, an NFC chip, a barcode, or an RFD chip directly at a hairdresser's or at a point of sale (POS) of hair treatment agents.

Alternatively, the app, in particular if it is to be installed on a smart terminal, can be downloaded via an Internet sales platform integrated in the respective operating system of the smart terminal. In the case of a smart terminal with the "Apple iOS" operating system, this sales platform can be the "App Store" for example, or in the case of a smart terminal with the "Android" operating system it can be the "Google Play Store".

In one embodiment the QR code, the NFC chip, the barcode or the RFID chip contains a web link which leads the user of the method to a web page from where the user of the method can download the app.

It is also preferred if the content of hair constituent determined in the method is output in a relative indication (very low, low, normal, high, and very high).

Alternatively or additionally, the associated hair state can be output in a relative indication (very very brittle, very brittle, slightly brittle, and normal).

The content can be output optically, for example by employing a display device of the (mobile) data processing device, or acoustically, for example by employing a voice message over a loudspeaker.

In a particularly preferred embodiment of the method the individual treatment advice comprises the recommendation of bleaching agents and/or hair colorants and/or haircare products and/or styling products.

The recommendation here can include the display or specification of a specific product name of a hair treatment agent, in particular of a bleaching agent and/or hair colorant and/or haircare product and/or styling product. Alternatively, the recommendation can include the display or specification of a product line or range, in particular a bleaching agent line/range and/or hair colorant line/range and/or haircare product line/range and/or styling product line/range, of a manufacturer.

If values deviating from the usual values are determined for the content of one or more amino acids, suitable haircare products, such as rinse-out treatments or conditioners, which contain protein hydrolysates can be recommended, for example. The protein hydrolysates preferably contain the amino acid(s) of which the content deviated from the usual values.

If values deviating from the usual values are determined for the content of one or more lipids, suitable haircare products, such as rinse-out treatments or conditioners, which contain lipids can be recommended, for example. The lipids used in the haircare products preferably comprises the lipid(s) of which the content deviated from the usual values.

If a value deviating from the usual values is determined for the content of 18-methyl eicosanoic acid, suitable haircare products, such as rinse-out treatments or conditioners, which contain cationically modified proteins, proteolipids and/or cationic silicones can be recommended. 18-methyl eicosanoic acid is bound in the hair as thioester and is responsible for the hydrophobic protective film of the hair. If the determined value for 18-methyl eicosanoic acid is lower than usual, the hair is too hydrophilic. By using cationically modified proteins, proteolipids and/or cationic silicones, the hair state in respect of the hydrophilicity of the surface of the hair can be improved.

In an alternative embodiment of the method the individual treatment advice includes a recommendation to abstain for a certain period of time from bleaching and/or oxidative dyeing and/or permanent deformation processes and/or heat treatments.

The term "permanent deformation process" includes all processes for curling straight hair or straightening curly hair. These can be permanent waving processes or chemical straightening processes. Besides the use of chemicals, heat treatments can also undesirably increase or reduce the content of certain hair constituents. Accordingly, the individual treatment advice may include a recommendation to abstain from heat treatments, such as the use of hair curlers or straightening irons, for a certain period of time.

Alternatively, when performing the method for determining an individualized hair treatment during a heat treatment, the individual treatment advice mat include a recommendation to terminate the heat treatment within a certain period of time, for example immediately, or to interrupt it for a certain period of time, for example a few minutes. In this case, the individualized hair treatment advice may be oriented towards the determined water content of the hair.

In a further embodiment as contemplated herein the individual treatment advice may include a dosing recommendation for a bleaching and/or an oxidative dyeing and/or a prediction of the result of a bleaching and/or oxidative dyeing.

If the content of melanin is determined, the individual treatment advice may include the recommendation of a bleaching agent or oxidative dye optimised in respect of the oxidising agent content.

In the case of a bleaching or oxidative dyeing of hair, the cuticle layer of the hair is opened in an alkali medium, and a hydrogen peroxide cocktail dosed to a varying degree—depending on the desired bleaching or lightening result—dissolves the melanin to a greater or lesser extent. The hair is made all the lighter, the more highly dosed is the hydrogen peroxide. Bleaching or oxidative dyeing processes always damage the hair noticeably on account of this mode of action. The higher is the concentration of the hydrogen peroxide and the longer is the reaction time, the greater is the damage. A bleaching or lightening agent adapted to the desired bleaching or lightening result and to the content of melanin in the hair of the individual can reduce the extent of the hair damage.

Conversely, with known melanin content of the hair of the individual, the result of a bleaching and/or oxidative dyeing can be predicted. Users increasingly wish to see a realistic impression of how their hair will look after a bleaching or (oxidative) dyeing before the bleaching or (oxidative) dyeing is actually performed. Many providers of bleaching or (oxidative) dyeing processes therefore offer color consultation apps. For example, hair colors can be tested beforehand in real time with the "Schwarzkopf Frisur-Styleguide" app. To this end, the user downloads the app on a smart terminal and records a photo of their head using the front camera. The software of the app identified the face and head shape. The user then selects a specific bleaching product or (oxidative) coloring product and the display device of the smart terminal displays how the user will look once this bleaching or (oxidative) dyeing has been performed.

In order to predict the bleaching or dyeing result, the starting hair color is firstly determined, and then the bleaching or dyeing result is calculated on the basis of the specific bleaching or coloring product selected by the user. Since the composition of hair influences the bleaching or dyeing result, the method for determining an individualized hair treatment provides better, in particular more realistic predictions of a result of a bleaching and/or (oxidative) dyeing.

In a further, advantageous embodiment of the method, the individual treatment advice lies in encouraging or discouraging the individual to/from using hair treatment products that the user of the method and/or the individual identifies on the basis of QR codes, NFC chips, barcodes or RFID chips.

In this embodiment of the method the user of the method, for example a hairdresser or any person at the point of sale of hair treatment agents, once the state of the hair has been determined by ascertaining the content of at least one hair constituent, can determine suitable or unsuitable hair treatment agents via QR codes, NFC chips, barcodes or RFID chips, which for example are attached to hair treatment agents themselves or to the storage location thereof, for example to the shelf in the hairdresser's or at the point of sale of hair treatment agents.

QR codes, NFC chips, barcodes or RFID chips make it possible to transmit information wirelessly.

An optoelectronically readable marking consisting of parallel lines and gaps of different widths is understood to be a barcode. The data in a barcode is read automatically by optical readers, such as barcode readers (scanners) or cameras and is further processed electronically. May smart terminals comprise software that makes it possible to detect the code information using the digital camera of the smart terminal and to display this immediately in decoded form to the user.

A QR (quick response) code is a two-dimensional code that of a square matrix formed of black and white squares which display the coded data in binary form. Smart terminals usually have an installed camera. Once the QR code has been photographed, the QR code is read/interpreted with the aid of software.

NFC chips and RFID chips are transmitter-receiver systems. In this case at least one communication partner must be active, i.e. must prompt the communication. The other partner can be a chip without power supply, for example. This passive part is also referred to as a transponder (=transmitter & responder). Besides the active-passive communication for example between a smart terminal as active communication partner and a transponder/chip, active-active communication is also possible.

The coupling/excitation occurs by magnetic alternating fields with low range generated by the active communication partner or by high-frequency radio waves. Thus, not only is data transmitted, but the transponder is also supplied with energy. The active communication partner, for example a smart terminal, contains a software that controls the actual reading process, and what is known as middleware with interfaces for further (mobile) data processing devices and/or databases.

RFID ("radio-frequency identification") functions via radio waves. RFID technology comprises a very broad offering of various chips and readers which differ in essence by storage capacity, production method, cost, frequency range and by the distance range.

NFC ("near field communication") is a standardised specialisation of RFID technology and was developed specifically for data transmission over short distances (max. 10 cm).

QR codes, NFC chips, barcodes or RFID chips can contain information for example regarding for which state of hair the respective hair treatment agent is suitable or unsuitable.

The individual hair treatment advice can also consist for example in determining the chemical composition of a hair treatment agent, in particular a bleaching agent, a hair dye, a haircare product and/or hair styling product.

In an alternative embodiment of the method the individual treatment advice lies in encouraging the individual to use bleaching agents and/or dyes and/or care products that are prepared individually for the individual and in initiating an ordering process, preferably by calling up a web page of a manufacturer of individual bleaching agents and/or individual dyes and/or individual care products.

Customers increasingly wish to obtain a product tailored individually to their own requirements. This can be a product produced especially for the customer or what is known as a "mass customized" product. In the case of a "mass customized" product, however, individualization can be achieved by varying just a few features of a product, although these features are considered to be key features by the customer. These "mass customized" products are preferably based on the concept of modularization, that is to say the product can be composed individually from various modules/building blocks.

There are often numerous dependencies between the multiple different features/ingredients of a product, and these can be expressed as "commands" or "restraints". In order to obtain a clear product definition, it may be advantageous for the ordering process to proceed with the aid of a product configurator. This configurator aids the customer in their selection of the features/ingredients and indicates the reliable/unreliable feature combinations, wherein the latter then are unavailable for selection.

In the case of bleaching agents, dyes, care products and styling products for hair, the relevant product features in particular include the chemical ingredients of the agents, the physical properties of the agents, and the type of formulation of the agents. With the aid of a product configurator, the selection of chemically and/or physically incompatible ingredients or the selection of ingredients unsuitable for the determined hair state can be avoided. Conversely, the selection of ingredients suitable for the determined hair state can be stipulated or proposed by the product configurator.

It is also preferred that the individual treatment advice is stored and is used during the subsequent course of the process for a long-term recommendation.

It can also be preferred for the individual treatment advice to consist in the recommendation of dietary supplements. The absence or low content of a hair constituent, in particular of one or more amino acids, can be a cause for an undesirable hair state. An absence or low content of cysteine, in particular L-cysteine, thus leads to brittle hair. L-cysteine is formed in the lever from L-serine and L-methionine. Thus, following the determination of a low content of cysteine in the hair, the treatment advice may lie in the recommendation of the administration of cysteine, serine and/or methionine, in particular the L-forms of these amino acids.

In a further embodiment a data comparison is performed between the (mobile) data processing device, in particular the smart terminal, and data that is stored in a cloud, before the recommendation is output to the user. This data can be, for example, data from users having the same or similar hair compositions (in particular contents of hair constituent) and possibly further identical or similar parameters (age, gender, behaviour patterns, etc.) and the recommendations/measured derived on that basis. By including values obtained from experience, for example in respect of the success of a treatment, the assessment of a suitability of a treatment advice/recommendation can be confirmed or modified for other users. It can thus be made possible for the user to always be provided with an optimal recommendation.

In various exemplary embodiments the individual treatment advice may comprise the recommendation to seek a hairdresser. In various exemplary embodiments a booking process can be initiated directly via the software/app that determines the individual treatment advice. To this end, the contact data of hairdressers can be stored in the software/app for example and can be displayed to the user. In addition, the selection can be limited via filters, such as post code. In various exemplary embodiments an appointment can be booked directly via the software/app. Alternatively, a hairdressing appointment can be booked via a separate software/app, for example Treatwell.

In a particularly preferred embodiment the wave of the hair is determined in addition to the determination of a hair constituent of the hair, and this is taken into consideration in the individual treatment advice.

In a particularly preferred embodiment the thickness of the hair is determined in addition to the determination of a hair constituent of the hair, and this is taken into consideration in the individual treatment advice.

Besides the content of constituent of the hair, further properties of the hair have an influence on the success of a treatment of the hair. In particular, the wave and/or the thickness of hair can thus influence the success of a treatment of the hair. The wave and/or thickness of hair in particular influences the treatment of hair with care agents.

The values for the wave and/or thickness of hair can be determined for example by employing suitable methods by the smart terminal on which the method for determining an individualized hair treatment is carried out.

The wave of hair can be determined for example with the aid of image editing and image processing methods. To this end, the user of the method photographs at least part of the hair of the individual. Suitable image editing and image processing programs, such as "ImageJ" determine the linear portion in the image with the aid of suitable plug-ins. Straight hair leads to a high portion of linearity, strongly waved hair leads to a low portion of linearity. The degree of waviness can preferably be specified in "wave %".

The image editing and image processing program for determining the wave can be part of the app for carrying out the method for individualized hair treatment. Alternatively, the determination of the wave with the aid of image editing and image processing methods can be carried out by employing separate methods. The separate method is performed advantageously by an app that is on the mobile data processing device, in particular the smart terminal, which is used to carry out the method for individualized hair treatment.

The wave can be determined via separate methods which are not associated with the method for determining an individualized hair treatment, or can also be determined empirically.

The information regarding wave can be provided via a suitable interface, for example an input window, which opens on the smart terminal when the method for individualized hair treatment is being carried out. The input window can specify relative degrees of wave, such as "none at all", "hardly any", "light", "medium", "heavy", "very heavy", and the user of the method selects the wave determined subjectively. In the case of a wave percentage determined by a separate method, a specific numerical value, for example 20%, can be input.

The thickness can be determined for example with the aid of an accessory for smart terminals. To this end, a microscope attachment can be clamped over the lens of a smart terminal, for example. Examples of microscope attachments of this kind for smart terminals are the "Nurugo Micro" from the company Nurugo or "µPeek" from the manufacturer Scrona. The user of the method also determines the thickness of the hair of the individual before and after the recording of near-infrared and/or infrared and/or VIS and/or Raman spectra of the hair of the individual (step d). To this end, the user photographs 2 to 20, preferably 3 to 15, and particularly preferably 5 to 10 different hairs together with a size reference with the aid of a microscope attachment. The average hair thickness of the individual is determined using an evaluation software that can be integrated in the app for carrying out the method for individualized hair treatment.

A further alternative method for determining the hair thickness which can be performed with suitable accessory by a smart terminal includes the refraction of laser light.

The hair thickness can be determined via separate methods which are not associated with the method for determining an individualized hair treatment, or can also be determined empirically.

The information regarding hair thickness can be provided via a suitable interface, for example an input window, which opens on the smart terminal when the method for individualized hair treatment is being carried out. The input window can specify relative degrees of hair thickness, such as "thin", "normal" and "thick", and the user of the method selects the hair thickness determined subjectively. In the case of an absolute hair thickness determined by a separate method, a numerical value, for example 80 µm, can be input.

For optimal care, thick hair and (very) heavily waved hair requires hair treatment agents having a high proportion of fat-containing or oil-containing ingredients, whereas haircare products having a low portion of fat-containing or oil-containing ingredients are advantageous for thin and/or straight hair.

In the case of bleaching and oxidative dyeing, the use of hydrogen peroxide in a heavily alkaline medium leads in most cases to damage of the hair treated in this way. In order to avoid or to reduce damage, agents for bleaching and/or for oxidative dyeing often also themselves contain care substances.

In a particularly preferred embodiment of the method, the individual treatment advice, depending on the determined state of the hair and depending on the thickness and/or the wave, includes a recommendation of bleaching agents and/or hair dyes and/or haircare products having a content of fat-containing or oil-containing ingredients adapted to the state of the hair and the thickness and/or wave of the hair.

Fat-containing and oil-containing ingredients in particular comprise glycerol monoesters, glycerol diesters or glycerol triesters with fatty acids, fatty acids, fatty alcohols, fatty acid mono esters or fatty acid diesters with fatty alcohols, vegetable oils, mineral oils, natural waves and synthetic waxes.

A further important property of the hair the influences the success of a treatment of the hair is the degree of greying. The degree of greying of hair has an effect in particular on the result of a bleaching or oxidative dyeing process.

The degree of greying can be determined via separate methods which are not associated with the method for determining an individualized hair treatment, or can also be determined empirically.

The degree of greying can be determined for example with the aid of image editing and image processing methods. To this end, the user of the method photographs at least part of the hair of the individual. The photographed part of the hair preferably includes large parts of the root area. Suitable image editing and image processing programs determine the degree of greying in the image. In a particularly preferred embodiment the determination of the degree of greying is an integral part of the method for individualized hair treatment and is performed by the app that carries out the method for determining an individualized hair treatment.

The information regarding the degree of greying can be provided via a suitable interface, for example an input window, which opens on the smart terminal when the method for individualized hair treatment is being carried out. The input window can specify the degree of greying in a percentage, such as "10%", "30%", "50%", "70%", "90%" and "100%", and the user of the method selects the degree of greying determined subjectively. In the case of a degree of greying percentage determined by a separate method, a numerical value, for example "68%", can be input.

Grey hairs usually take up the oxidation dye preliminary products used in oxidative dyeing to a lesser extent than hair that is rich in pigment. This leads to different coloring results depending on the degree of greying of the hair.

In individuals with a poor hair state, in particular individuals with (very) heavily oxidatively damaged hair and no or a low degree of greying, the individual treatment advice may therefore consist in discouraging the individual from using bleaching agents and/or dyes and in advising the individual to use coloring processes that do not involve oxidative treatment, for example tinting or intense tinting processes.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for the individualized treatment of hair, the method comprising:
   a) determining a content of hair constituent of a number of samples of hair with a different hair state by a chromatographic or colorimetric process;
   b) recording near-infrared and/or infrared and/or VIS and/or Raman spectra of the samples of hair with a different hair state;
   c) creating a calibration model which produces a correlation between near-infrared and/or infrared and/or VIS and/or Raman spectra and the content of hair constituent;
   d) recording a near-infrared and/or an infrared and/or a VIS and/or a Raman spectrum of hair of an individual;
   e) determining the state of the hair of the individual on the basis of the calibration model; and
   f) outputting individual treatment advice regarding the hair of the individual depending on the determined hair state, wherein the hair constituent is selected from the group of amino acids, lipids, melanins, water and mixtures thereof.

2. The method according to claim 1, wherein the calibration model from steps a) to c) is present in the form of stored information on a local data carrier or in a cloud.

3. The method according to claim 1, wherein step d) is performed at a hairdresser's, at a point of sale (POS) of hair treatment agents, or in the private field.

4. The method according to claim 1, wherein step d) is controlled by a smart terminal.

5. The method according to claim 4, wherein step d) is controlled by the smart terminal via a previously installed app.

6. The method according to claim 5, wherein the previously installed app is downloaded via a QR code, an NFC chip, a barcode or an RFID chip directly at a hairdresser's or at a point of sale (POS) of hair treatment agents.

7. The method according to claim 1, wherein the hair state is a hair state selected from the group of brittle, lacklustre, oxidatively damaged, heat-damaged, chemically damaged, dry, moist, greasy, hydrophilic, high in melanin, low in melanin, normal and combinations thereof.

8. The method according to claim 1, wherein the calibration model takes into account further factors.

9. The method according to claim 8, wherein the further factors comprise categorical factors.

10. The method according to claim 9, wherein the categorical factors comprise ethnicity of the individual, age of the individual and/or hair color of the individual.

11. The method according to claim 1, wherein the individual treatment advice comprises a recommendation of hair treatment agents.

12. The method according to claim 11, wherein hair treatment agents comprise bleaching agents and/or hair dyes and/or haircare products and/or styling products.

13. The method according to claim 1, wherein the individual treatment advice comprises a recommendation to abstain for a certain period of time from bleaching and/or oxidative dyeing and/or permanent deformation processes and/or heat treatments.

14. The method according to claim 1, wherein the individual treatment advice comprises a recommendation to lighten and/or oxidatively dye the hair color only by a maximum number of shades for a certain period of time.

15. The method according to claim 1, wherein the individual treatment advice comprises a dosing recommendation for a bleaching and/or an oxidative dyeing and/or a prediction of the result of a bleaching and/or oxidative dyeing.

16. The method according to claim 1, wherein the individual treatment advice lies in encouraging or discouraging the individual to/from using hair treatment products that the individual identifies on the basis of QR codes, NFC chips, barcodes or RFID chips.

17. The method according to claim 1, wherein the individual treatment advice lies in encouraging the individual to use bleaching agents and/or hair dyes and/or haircare products that are prepared individually for the individual and in initiating an ordering process.

18. The method according to claim 1, wherein, in addition to the state of the hair, the wave thereof is determined and this is taken into consideration in the individual treatment advice.

19. The method according to claim 1, wherein, in addition to the state of the hair, the thickness thereof is determined and this is taken into consideration in the individual treatment advice.

20. The method according to claim 1, wherein, in addition to the state of the hair, the degree of greying thereof is determined and this is taken into consideration in the individual treatment advice.

* * * * *